United States Patent
Schaefer et al.

(10) Patent No.: US 8,323,306 B2
(45) Date of Patent: *Dec. 4, 2012

(54) MICROCOIL VASO-OCCLUSIVE DEVICE WITH MULTI-AXIS SECONDARY CONFIGURATION

(75) Inventors: Dean Schaefer, Aliso Viejo, CA (US); Brian J. Cox, Laguna Niguel, CA (US); George R. Greene, Jr., Costa Mesa, CA (US); David A. Ferrera, Manhattan Beach, CA (US); Matthew Fitz, Encinitas, CA (US); Robert F. Rosenbluth, Laguna Niguel, CA (US)

(73) Assignee: MicroVention, Inc., Tustin, CA (US)

( * ) Notice: Subject to any disclaimer, the term of this patent is extended or adjusted under 35 U.S.C. 154(b) by 465 days.

This patent is subject to a terminal disclaimer.

(21) Appl. No.: 11/398,081

(22) Filed: Apr. 5, 2006

(65) Prior Publication Data
US 2006/0184195 A1    Aug. 17, 2006

Related U.S. Application Data

(63) Continuation of application No. 10/247,231, filed on Sep. 19, 2002, now Pat. No. 7,029,486, which is a continuation-in-part of application No. 10/043,947, filed on Jan. 11, 2002, now Pat. No. 7,033,374, which is a continuation-in-part of application No. 09/671,021, filed on Sep. 26, 2000, now Pat. No. 6,605,101.

(51) Int. Cl.
*A61M 29/00* (2006.01)
*A61F 2/06* (2006.01)

(52) U.S. Cl. ............... 606/191; 606/198; 623/1.1

(58) Field of Classification Search .......... 606/191, 606/194, 198, 200, 151; 604/52, 104; 623/1, 623/11, 12

See application file for complete search history.

(56) References Cited

U.S. PATENT DOCUMENTS

| 4,551,132 A | 11/1985 | Pásztor et al. |
| 4,663,358 A | 5/1987 | Hyon et al. |

(Continued)

FOREIGN PATENT DOCUMENTS
DE    19647280 A1    11/1996
(Continued)

OTHER PUBLICATIONS

Gianturco. et al.; Mechanical Devices for Arterial Occlusion:, Am. J. Roentgenology, 124:428-435, Jul. 1975.

(Continued)

*Primary Examiner* — Gary Jackson
*Assistant Examiner* — Michael Mendoza
(74) *Attorney, Agent, or Firm* — Inskeep IP Group, Inc.

(57) ABSTRACT

A vaso-occlusive device includes a microcoil formed into a minimum energy state secondary configuration comprising a plurality of curved segments, each defining a discrete axis, whereby the device, in its minimum energy state configuration, defines multiple axes. Confinement of the device within an aneurysm causes it to assume a three-dimensional configuration with a higher energy state than the minimum energy state. Because the minimum energy state configuration of the device is larger (in at least one dimension) than the aneurysm, the deployed device is constrained by its contact with the walls of the aneurysm from returning to its minimum energy state configuration. The engagement of the device with the aneurysm wall minimizes shifting or tumbling due to blood flow.

11 Claims, 6 Drawing Sheets

U.S. PATENT DOCUMENTS

| | | | |
|---|---|---|---|
| 4,739,768 A | 4/1988 | Engelson | |
| 4,795,741 A | 1/1989 | Leshchiner et al. | |
| 4,819,637 A | 4/1989 | Dormandy, Jr. et al. | |
| 4,884,579 A | 12/1989 | Engelson | |
| 4,957,501 A | 9/1990 | Lahille et al. | |
| 4,994,069 A | 2/1991 | Ritchart et al. | |
| 5,108,407 A | 4/1992 | Geremia et al. | |
| 5,122,136 A | 6/1992 | Guglielmi et al. | |
| 5,133,731 A | 7/1992 | Butler et al. | |
| 5,226,911 A | 7/1993 | Chee et al. | |
| 5,234,437 A | 8/1993 | Sepetka | |
| 5,258,042 A | 11/1993 | Mehta | |
| 5,261,916 A | 11/1993 | Engelson | |
| 5,304,194 A | 4/1994 | Chee et al. | |
| 5,304,195 A | 4/1994 | Twyford, Jr. et al. | |
| 5,312,415 A | 5/1994 | Palermo | |
| 5,314,444 A * | 5/1994 | Gianturco | 606/195 |
| 5,342,387 A | 8/1994 | Summers | |
| 5,350,397 A | 9/1994 | Palermo et al. | |
| 5,350,398 A | 9/1994 | Pavcnik et al. | |
| 5,382,259 A | 1/1995 | Phelps et al. | |
| 5,382,260 A | 1/1995 | Dormandy, Jr. et al. | |
| 5,413,791 A | 5/1995 | Rhee et al. | |
| 5,423,829 A | 6/1995 | Pham et al. | |
| 5,476,472 A | 12/1995 | Dormandy, Jr. et al. | |
| 5,522,822 A | 6/1996 | Phelps et al. | |
| 5,522,836 A | 6/1996 | Palermo | |
| 5,525,334 A | 6/1996 | Ito et al. | |
| 5,527,338 A | 6/1996 | Purdy | |
| 5,536,274 A | 7/1996 | Neuss | |
| 5,549,624 A | 8/1996 | Mirigian et al. | |
| 5,578,074 A | 11/1996 | Mirigian | |
| 5,580,568 A | 12/1996 | Greff et al. | |
| 5,582,619 A | 12/1996 | Ken | |
| 5,624,461 A | 4/1997 | Mariant | |
| 5,639,277 A | 6/1997 | Mariant et al. | |
| 5,645,558 A | 7/1997 | Horton | |
| 5,645,564 A | 7/1997 | Northrup et al. | |
| 5,649,949 A | 7/1997 | Wallace et al. | |
| 5,658,308 A | 8/1997 | Snyder | |
| 5,676,697 A | 10/1997 | McDonald | |
| 5,690,667 A | 11/1997 | Gia | |
| 5,690,671 A | 11/1997 | McGurk et al. | |
| 5,700,258 A | 12/1997 | Mirigian et al. | |
| 5,718,711 A | 2/1998 | Berenstein et al. | |
| 5,725,546 A | 3/1998 | Samson | |
| 5,749,891 A | 5/1998 | Ken et al. | |
| 5,766,219 A | 6/1998 | Horton | |
| 5,797,953 A | 8/1998 | Tekulve | |
| 5,814,062 A | 9/1998 | Sepetka et al. | |
| 5,868,754 A | 2/1999 | Levine et al. | |
| D407,818 S | 4/1999 | Mariant et al. | |
| 5,891,058 A | 4/1999 | Taki et al. | |
| 5,895,378 A | 4/1999 | Nita | |
| 5,911,731 A | 6/1999 | Pham et al. | |
| 5,911,737 A | 6/1999 | Lee et al. | |
| 5,957,948 A | 9/1999 | Mariant | |
| 5,980,514 A | 11/1999 | Kupiecki et al. | |
| 5,989,242 A | 11/1999 | Saadat et al. | |
| 6,004,448 A | 12/1999 | Martyak | |
| 6,010,498 A | 1/2000 | Guglielmi | |
| 6,013,084 A | 1/2000 | Ken et al. | |
| 6,015,424 A | 1/2000 | Rosenbluth et al. | |
| D421,304 S | 2/2000 | Mariant et al. | |
| 6,022,369 A | 2/2000 | Jacobsen et al. | |
| 6,024,765 A | 2/2000 | Wallace et al. | |
| 6,033,423 A | 3/2000 | Ken et al. | |
| 6,063,100 A | 5/2000 | Diaz et al. | |
| 6,068,644 A | 5/2000 | Lulo et al. | |
| D427,680 S | 7/2000 | Mariant et al. | |
| 6,090,125 A | 7/2000 | Horton | |
| 6,096,034 A | 8/2000 | Kupiecki et al. | |
| 6,102,933 A | 8/2000 | Lee et al. | |
| 6,164,198 A | 12/2000 | McGurk et al. | |
| 6,165,194 A | 12/2000 | Denardo | |
| 6,165,198 A | 12/2000 | McGurk et al. | |
| 6,171,326 B1 | 1/2001 | Ferrera et al. | |
| 6,176,240 B1 | 1/2001 | Nikolchev et al. | |
| 6,193,728 B1 | 2/2001 | Ken et al. | |
| RE37,117 E | 3/2001 | Palermo | |
| 6,231,586 B1 | 5/2001 | Mariant | |
| 6,280,457 B1 | 8/2001 | Wallace et al. | |
| 6,322,567 B1 | 11/2001 | Mittelstadt et al. | |
| 6,322,576 B1 | 11/2001 | Wallace et al. | |
| 6,432,134 B1 | 8/2002 | Anson et al. | |
| 6,478,773 B1 | 11/2002 | Gandhi et al. | |
| 6,500,190 B2 | 12/2002 | Greene, Jr. et al. | |
| 6,585,756 B1 | 7/2003 | Strecker | |
| 6,589,265 B1 | 7/2003 | Palmer et al. | |
| 6,605,101 B1 | 8/2003 | Schaefer et al. | |
| 6,635,068 B1 | 10/2003 | Dubrul et al. | |
| 6,635,069 B1 | 10/2003 | Teoh et al. | |
| 6,638,291 B1 | 10/2003 | Ferrera et al. | |
| 6,656,218 B1 * | 12/2003 | Denardo et al. | 623/1.15 |
| 6,860,893 B2 | 3/2005 | Wallace et al. | |
| 6,929,654 B2 | 8/2005 | Teoh et al. | |
| 6,984,240 B1 | 1/2006 | Ken et al. | |
| 7,066,904 B2 | 6/2006 | Rosenthal et al. | |
| 7,229,454 B2 | 6/2007 | Tran et al. | |
| 2002/0107534 A1 | 8/2002 | Schaefer et al. | |
| 2002/0128671 A1 | 9/2002 | Wallace et al. | |
| 2003/0120302 A1 * | 6/2003 | Minck et al. | 606/200 |
| 2005/0192618 A1 | 9/2005 | Porter | |
| 2005/0192621 A1 | 9/2005 | Wallace et al. | |

FOREIGN PATENT DOCUMENTS

| | | |
|---|---|---|
| EP | 0739605 B1 | 10/1996 |
| EP | EP 0739605 B1 | 8/1998 |
| JP | 7155331 | 6/1995 |
| JP | 8317992 | 12/1996 |
| WO | WO 94/11051 A1 | 5/1994 |
| WO | WO9411051 A1 | 5/1994 |
| WO | WO9802100 A1 | 1/1998 |
| WO | WO9817183 A1 | 4/1998 |
| WO | WO 99/09893 A1 | 3/1999 |
| WO | WO9909893 A1 | 3/1999 |
| WO | 00/21443 A1 | 4/2000 |
| WO | WO0021443 A1 | 4/2000 |
| WO | WO 00/74577 A1 | 12/2000 |
| WO | WO0074577 A1 | 12/2000 |
| WO | WO 01/45571 A1 | 6/2001 |
| WO | WO0145571 A1 | 6/2001 |
| WO | WO 01/93780 A3 | 12/2001 |
| WO | WO0193780 A2 | 12/2001 |
| WO | WO 02/32325 A1 | 4/2002 |
| WO | WO0232325 A1 | 4/2002 |
| WO | WO03039376 A1 | 5/2003 |

OTHER PUBLICATIONS

Anderson, et al.; "Transcatheter Intravascular Coil Occlusion . . . "; Am. J. Roentgennol 129:795-798, Nov. 1977.

Anderson, et al.; "'Mini' Gianturco Stainless Steel Coils for . . . "; Radiology, 132: 301-303, Aug. 1979.

Brunelle, et al.; "Micro Stainless Steel Coils for Transcatheter . . . "; Pediatric Radiology 13:332-334, 1983.

Lund, et al.: "Detachable Steel Spring Coils for Vessel Occlusion"; Radiology 155:530, 1985.

Yang, et "Platinum Wire: A new Transvascular Embolic Agent"; AJNR 9:547-550, May/Jun. 1988.

Malek, et al.; "Treatment of an Intracranial Aneurysm . . . "; Neurosurgery, vol. 44, No. 5, May 1999.

Cloft, et al.; "Use of Three-dimensional Gugliemi Detachable . . . "; American Society Neuroradiology 21:1312-1314, Aug. 2000.

European Patent Office, Examination Report mailed Mar. 3, 2011 in European Patent Application No. 09015616.7, 4 pages.

European Patent Office, Examination Report mailed May 3, 2010 in European Patent Application No. 03707353.3, 4 pages.

European Patent Office, Supplementary European Search Report mailed Feb. 15, 2010 in European Patent Application No. 09015616.7, 3 pages.

United States Patent and Trademark Office, Office Action mailed Jan. 26, 2010 in U.S. Appl. No. 11/398,082, 8 pages.

Japan Patent Office, Final Office Action mailed Dec. 8, 2009 in Japanese Patent Application No. 2003559346, 6 pages.

European Patent Office, Decision to Grant mailed Nov. 26, 2009 in European Patent Application No. 01986219.2, 2 pages.
United States Patent and Trademark Office, Final Office Action mailed Aug. 6, 2009 in U.S. Appl. No. 11/398,082, 6 pages.
Japan Patent Office, Office Action mailed Jan. 27, 2009 in Japanese Patent Application No. 2003-559346, 4pages.
United States Patent and Trademark Office, Office Action mailed Jan. 9, 2009 in U.S. Appl. No. 11/398,082, 11 pages.
SIPO, Office Action mailed Jun. 21, 2009 in Chinese Patent Application No. 2007100052684, 3 pages.
SIPO, Office Action mailed Oct. 21, 2008 in Chinese Patent Application 2007100052684, 4 pages.
United States Patent and Trademark Office, Office Action mailed Oct. 6, 2008 in U.S. Appl. No. 11/398,082, 6 pages.
European Patent Office, Examination Report mailed Aug. 1, 2008 in European Patent Application No. 01986219.2, 3 pages.
SIPO, Office Action mailed Jun. 22, 2008 in Chinese Patent Application No. 018237738, 8 pages.
Japan Patent Office, Notice of Allowance mailed Mar. 6, 2008 in Japanese Patent Application No. 2003541472, 3 pages.
IP Australia, Notice of Acceptance mailed Feb. 13, 2008 in Australian Patent Application No. 2002236676, 3 pages.
Canadian Intellectual Property Office, Notice of Allowance mailed Feb. 13, 2008 in Canadian Application No. 2,466,017, 1page.
European Patent Office, Examination Report mailed Dec. 27, 2007 in European Patent Application No. 01986219.2, 3 pages.
Japan Patent Office, Examination Report mailed Oct. 11, 2007 in Japanese Patent Application No. 2003541472, 4 pages.
United States Patent and Trademark Office, Notice of Allowance mailed Aug. 30, 2007 in U.S. Appl. No. 10/638,813, 3 pages.
IP Australia, Examiner's Report mailed Jul. 19, 2007 in Australian Patent Application No. 2002236676, 2 pages.
United States Patent and Trademark Office, Office Action mailed Jul. 11, 2007 in U.S. Appl. No. 10/755,249, 17 pages.
European Patent Office, Examination Report mailed Jun. 5, 2007 in European Patent Application No. 01986219.2, 4 pages.
United States Patent and Trademark Office, Office Action mailed Jan. 22, 2007 in U.S. Appl. No. 10/638,813, 2 pages.
United States Patent and Trademark Office, Office Action mailed Dec. 1, 2006 in U.S. Appl. No. 10/755,249, 30 pages.
United States Patent and Trademark Office, Final Office Action mailed Aug. 7, 2006 in U.S. Appl. No. 10/638,813, 2 pages.
United States Patent and Trademark Office, Notice of Allowance mailed Dec. 2, 2005 in U.S. Appl. No. 10/043,947, 3 pages.
United States Patent and Trademark Office, Notice of Allowance mailed Nov. 17, 2005 in U.S. Appl. No. 10/247,231, 3 pages.
WIPO, U.S. International Preliminary Examining Authority, International Preliminary Report on Patentability mailed Apr. 15, 2004 in International Patent Application No. PCT/US 03/00779, 7 pages.
WIPO, U.S. International Preliminary Examining Authority, Written Opinion mailed Jan. 27, 2004 in International Patent Application No. PCT/US 03/00779, 5 pages.
WIPO, U.S. International Preliminary Examining Authority, International Preliminary Report on Patentability mailed Aug. 27, 2003 in International Patent Application No. PCT/US 01/50970, 2 pages.
WIPO, U.S. International Search Authority, International Search Report mailed Jun. 30, 2003 in International Patent Application No. PCT/US 03/00779, 4 pages.
WIPO, U.S. International Search Authority, International Search Report and Written Opinion mailed Jun. 10, 2002 in International Patent Application No. PCT/US 01/50970, 3 pages.
Cloft, H.J. et al., "Use of Three-dimensional Guglielmi Detachable Coils in the Treatment of Wide-necked Cerebral Aneurysms," *American Journal of Neuroradiology*, vol. 21, Aug. 2000, 3 pages.
Tan, C.B. et al., "The Feasibility of Three-Dimensional Guglielmi Detachable Coil for Embolisation of Wide Neck Cerebral Aneurysms," *Interventional Neuroradiology*, vol. 6, 2000, 6 pages.
Malek, A.M., et al., "Treatment of an Intracranial Aneurysm Using a New Three-Dimensional-Shape Guglielmi Detachable Coil: Technical Case Report," *Neurosurgery*, vol. 44, No. 5, May 1999, 4 pages.
Yang, P.J., et al., "Platinum Wire: A New Transvascular Embolic Agent," American Journal of Neuroradiology, vol. 9, No. 3, American Society of Neuroradiology, Jun. 1988, 4 pages.
Lund, G., et al., "Detachable Steel Spring Coils for Vessel Occlusion," *Radiology*, vol. 155, 1985, 4 pages.
Brunelle, F., et al., ""Micro" Stainless Steel Coils for Transcatheter Vascular Occlusion in Children," *Pediatric Radiology*, vol. 13, 1983, 3 pages.
Anderson, J., et al., ""Mini" Gianturco Stainless Steel Coils for Transcatheter Vascular Occlusion," *Radiology*, vol. 132, Aug. 1979, 3 pages.
Anderson, J., et al., "Transcatheter Intravascular Coil Occlusion of Experimental Arteriovenous Fistulas," *American Journal of Roentgenology*, vol. 129, Nov. 1977, 4 pages.
Gianturco, C., et al., "Mechanical Devices for Arterial Occlusion," *American Journal of Roentgenology*, vol. 124, No. 3, Jul. 1975, 8 pages.

* cited by examiner

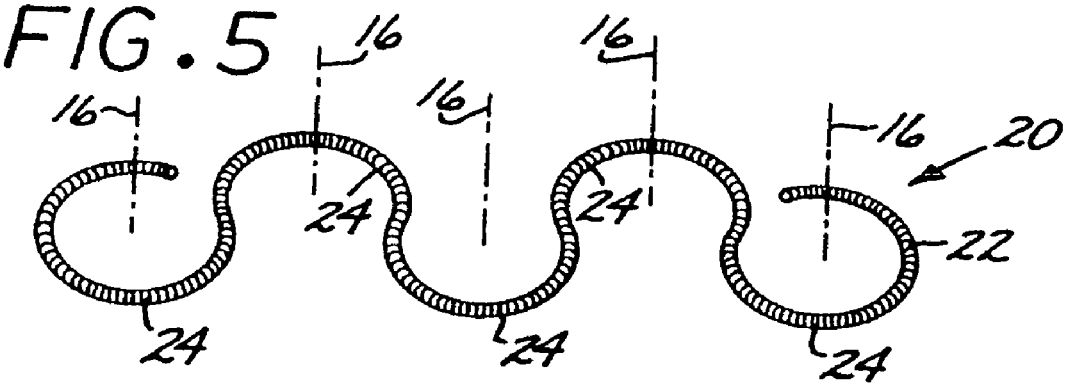
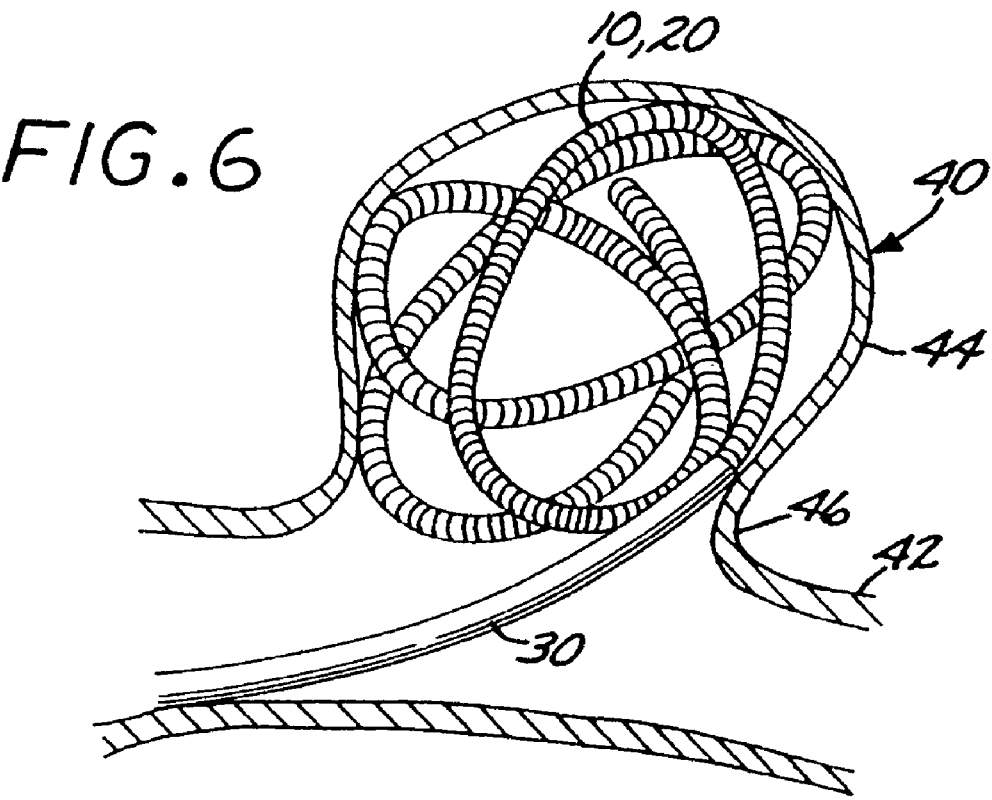

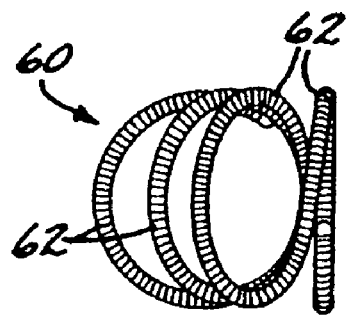
FIG. 8
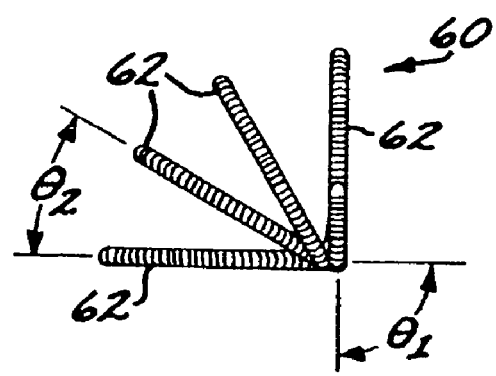
FIG. 9
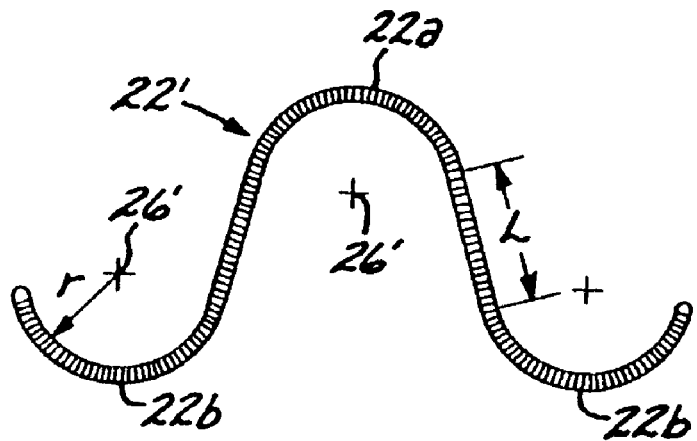
FIG. 10
FIG. 11
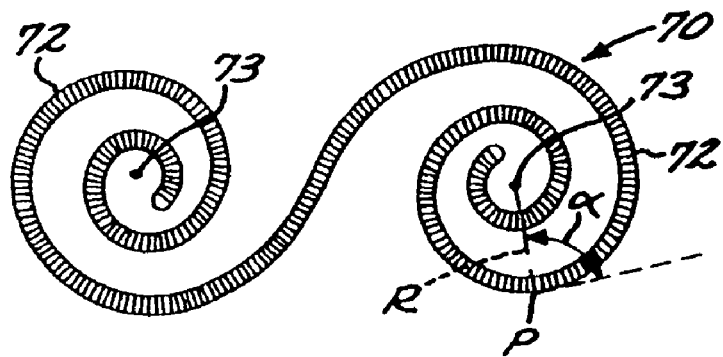

MICROCOIL VASO-OCCLUSIVE DEVICE WITH MULTI-AXIS SECONDARY CONFIGURATION

CROSS-REFERENCE TO RELATED APPLICATIONS

This application is a Continuation of co-pending application Ser. No. 10/247,231, filed Sep. 19, 2002; which is a Continuation-in-Part of co-pending application Ser. No. 10/043,947, filed Jan. 11, 2002, which is a Continuation-in-Part of application Ser. No. 09/671,021, filed Sep. 26, 2000, now U.S. Pat. No. 6,605, 101, issued Aug. 12, 2003; the disclosures of which are incorporated herein by reference.

FEDERALLY-SPONSORED RESEARCH OR DEVELOPMENT

Not Applicable

BACKGROUND OF THE INVENTION

This invention relates generally to the field of vascular occlusion devices and methods. More specifically, it relates to an apparatus and method for occluding a blood vessel by embolizing a targeted site (such as an aneurysm) in the blood vessel.

The embolization of blood vessels is desired in a number of clinical situations. For example, vascular embolization has been used to control vascular bleeding, to occlude the blood supply to tumors, and to occlude vascular aneurysms, particularly intracranial aneurysms. In recent years, vascular embolization for the treatment of aneurysms has received much attention. Several different treatment modalities have been employed in the prior art. U.S. Pat. No. 4,819,637—Dormandy, Jr. et al., for example, describes a vascular embolization system that employs a detachable balloon delivered to the aneurysm site by an intravascular catheter. The balloon is carried into the aneurysm at the tip of the catheter, and it is inflated inside the aneurysm with a solidifying fluid (typically a polymerizable resin or gel) to occlude the aneurysm. The balloon is then detached from the catheter by gentle traction on the catheter. While the balloon-type embolization device can provide an effective occlusion of many types of aneurysms, it is difficult to retrieve or move after the solidifying fluid sets, and it is difficult to visualize unless it is filled with a contrast material. Furthermore, there are risks of balloon rupture during inflation and of premature detachment of the balloon from the catheter.

Another approach is the direct injection of a liquid polymer embolic agent into the vascular site to be occluded. One type of liquid polymer used in the direct injection technique is a rapidly polymerizing liquid, such as a cyanoacrylate resin, particularly isobutyl cyanoacrylate, that is delivered to the target site as a liquid, and then is polymerized in situ. Alternatively, a liquid polymer that is precipitated at the target site from a carrier solution has been used. An example of this type of embolic agent is a cellulose acetate polymer mixed with bismuth trioxide and dissolved in dimethyl sulfoxide (DMSO). Another type is ethylene glycol copolymer dissolved in DMSO. On contact with blood, the DMSO diffuses out, and the polymer precipitates out and rapidly hardens into an embolic mass that conforms to the shape of the aneurysm. Other examples of materials used in this "direct injection" method are disclosed in the following U.S. Pat. No. 4,551, 132—Pásztor et al.; U.S. Pat. No. 4,795,741—Leshchiner et al.; U.S. Pat. No. 5,525,334—Ito et al.; and U.S. Pat. No. 5,580,568—Greff et al.

The direct injection of liquid polymer embolic agents has proven difficult in practice. For example, migration of the polymeric material from the aneurysm and into the adjacent blood vessel has presented a problem. In addition, visualization of the embolization material requires that a contrasting agent be mixed with it, and selecting embolization materials and contrasting agents that are mutually compatible may result in performance compromises that are less than optimal. Furthermore, precise control of the deployment of the polymeric embolization material is difficult, leading to the risk of improper placement and/or premature solidification of the material. Moreover, once the embolization material is deployed and solidified, it is difficult to move or retrieve.

Another approach that has shown promise is the use of thrombogenic microcoils. These microcoils may be made of a biocompatible metal alloy (typically platinum and tungsten) or a suitable polymer. If made of metal, the coil may be provided with Dacron fibers to increase thrombogenicity. The coil is deployed through a microcatheter to the vascular site. Examples of microcoils are disclosed in the following U.S. Pat. No. 4,994,069—Ritchart et al.; U.S. Pat. No. 5,122, 136—Guglielmi et al.; U.S. Pat. No. 5,133,731—Butler et al.; U.S. Pat. No. 5,226,911—Chee et al.; U.S. Pat. No. 5,304, 194—Chee et al.; U.S. Pat. No. 5,312,415—Palermo; U.S. Pat. No. 5,382,259—Phelps et al.; U.S. Pat. No. 5,382,260—Dormandy, Jr. et al.; U.S. Pat. No. 5,476,472—Dormandy, Jr. et al.; U.S. Pat. No. 5,578,074—Mirigian; U.S. Pat. No. 5,582,619—Ken; U.S. Pat. No. 5,624,461—Mariant; U.S. Pat. No. 5,639,277—Mariant et al.; U.S. Pat. No. 5,658, 308—Snyder; U.S. Pat. No. 5,690,667—Gia; U.S. Pat. No. 5,690,671—McGurk et al.; U.S. Pat. No. 5,700,258—Mirigian et al.; U.S. Pat. No. 5,718,711—Berenstein et al.; U.S. Pat. No. 5,891,058—Taki et al.; U.S. Pat. No. 6,013,084—Ken et al.; U.S. Pat. No. 6,015,424—Rosenbluth et al.; and Des. 427,680—Mariant et al.

While many prior art microcoil devices have met with some success in treating small aneurysms with relatively narrow necks, it has been recognized that the most commonly used microcoil vaso-occlusive devices achieve less than satisfactory results in wide-necked aneurysms, particularly in the cerebrum. This has led to the development of three-dimensional microcoil devices, such as those disclosed in U.S. Pat. No. 5,645,558—Horton; U.S. Pat. No. 5,911,731—Pham et al.; and U.S. Pat. No. 5,957,948—Mariant (the latter two being in a class of devices known as "three-dimensional Guglielmi detachable coils", or "3D-GDC's"). See, e.g., Tan et al., "The Feasibility of Three-Dimensional Guglielmi Detachable Coil for Embolisation of Wide Neck Cerebral Aneurysms," *Interventional Neuroradiology*, Vol. 6, pp. 53-57 (June, 2000); Cloft et al., "Use of Three-Dimensional Guglielmi Detachable Coils in the Treatment of Wide-necked Cerebral Aneurysms," *American Journal of Neuroradiology*, Vol. 21, pp. 1312-1314 (August, 2000).

The typical three-dimensional microcoil is formed from a length of wire that is formed first into a primary configuration of a helical coil, and then into a secondary configuration that is one of a variety of three-dimensional shapes. The minimum energy state of this type of microcoil is its three-dimensional secondary configuration. When deployed inside an aneurysm, these devices assume a three-dimensional configuration, typically a somewhat spherical configuration, that is at or slightly greater than, the minimum energy state of the secondary configuration. Because the overall dimensions of these devices in their non-minimum energy state configuration is approximately equal to or smaller than the interior dimensions of the aneurysm, there is nothing to constrain the device from shifting or tumbling within the aneurysm due to blood flow dynamics.

In some of these three-dimensional devices (e.g., U.S. Pat. No. 5,122,136—Guglielmi et al.), the secondary configuration is itself a helix or some similar form that defines a longitudinal axis. Devices with what may be termed a "longitudinal" secondary configuration form a three-dimensional non-minimum energy state configuration when deployed inside an aneurysm, but, once deployed, they have displayed a tendency to revert to their minimum energy state configurations. This, in turn, results in compaction due to "coin stacking" (i.e., returning to the secondary helical configuration), thereby allowing recanalization of the aneurysm.

There has thus been a long-felt, but as yet unsatisfied need for a microcoil vaso-occlusive device that has the advantages of many of the prior art microcoil devices, but that can be used effectively to treat aneurysms of many different sizes configurations, and in particular those with large neck widths. It would be advantageous for such a device to be compatible for use with existing guidewire and microcatheter microcoil delivery mechanisms, and to be capable of being manufactured at costs comparable with those of prior art microcoil devices.

SUMMARY OF THE INVENTION

Broadly, the present invention is a filamentous vaso-occlusive device that has a minimum energy state secondary configuration comprising a plurality of curved segments, whereby the device, in its minimum energy state secondary configuration, defines multiple axes and/or foci. More specifically, each segment defines either (1) a plane and an axis that is substantially perpendicular to the plane, or (2) a path around the surface of a sphere, wherein the path is defined by a unique locus located at the approximate center point of the sphere around which the path is generated, and by a radius extending from that locus that is equal to the radius of that sphere.

More specifically, the present invention is a vaso-occlusive device for embolizing a vascular site having a known maximum dimension (i.e., depth, width, or length), wherein the device comprises a filamentous structure formed into a minimum energy state secondary configuration comprising a plurality of curved segments, each having a diameter approximately equal to the known maximum dimension of the vascular site, and wherein the device, in its minimum energy state secondary configuration, has an overall length that is at least about twice, and preferably about three times the known maximum dimension of the vascular site.

In another aspect, the invention is a vaso-occlusive device for embolizing a vascular site having a known maximum dimension, comprising a filamentous structure having proximal and distal ends, wherein the filamentous structure is formed into a minimum energy state secondary configuration comprising a plurality of loops, each defining plane and a unique axis perpendicular to the plane, such that as a path is traced along the filamentous structure from the proximal end to the distal end, the path defines a closed-loop path segment around each of the axes, the path segments alternating between clockwise and counter-clockwise path segments around successive axes.

In still another aspect, the invention is a filamentous vaso-occlusive device having a minimum energy state secondary configuration comprising a plurality of tangentially-interconnected loops, each defining a plane and a unique axis perpendicular to the plane, wherein the device has a proximal end and a distal end and defines a substantially continuously-curved structure between the proximal and distal ends.

In a particular preferred embodiment, the present invention is an elongate microcoil structure having a minimum energy state secondary configuration that defines a plurality or series of tangentially-interconnected, substantially closed, non-overlapping loops, defining a plurality of separate axes. In one form of the preferred embodiment, the closed loops are substantially coplanar and define axes that are substantially parallel. That is, the planes defined by the segments are themselves substantially coplanar. In another form of the preferred embodiment, each pair of adjacent loops defines a shallow angle, whereby their respective axes define an angle of not more than about 90°, and preferably not more than about 45°, between them. A further form of the preferred embodiment has the tangential loops arranged so that the axis defined by each loop is orthogonal to a unique radius of a circle, the radii being separated by a fixed angle of arc. In still another form of the preferred embodiment, the loops, instead of being tangential, overlap. In any of these forms, the loops may be of substantially uniform diameter, or they may be of different diameters. For example, the first and/or last loop in the series may be of a smaller diameter than the other loops, or the loops may be in a series of loops of progressively decreased diameter, optionally with an additional small-diameter loop preceding the largest diameter loop.

In first alternative embodiment, the microcoil structure has a minimum energy state secondary configuration that defines a wave-form like structure comprising a longitudinal array of laterally-alternating open loops defining a plurality of separate axes. In a specific construction of this embodiment, the wave-form like structure defines a substantially sinusoidal waveform wherein each of the maxima and minima of the waveform defines an arc of radius r, and wherein each arc is connected to an adjacent arc by a straight section of length L, wherein L is less than about 2r. As in the preferred embodiment, the alternative embodiment may be in a first form in which the loops are substantially coplanar and their respective axes are substantially parallel, or in a second form in which each pair of adjacent loops defines a shallow angle, whereby their respective axes define an angle of not more than about 90°, and preferably not more than about 45°, between them.

In a second alternative embodiment, the microcoil structure, in its secondary configuration, forms a series of tangential closed loops, preferably either substantially circular or elliptical, wherein the entire structure subtends a first angle of arc, and wherein each adjacent pair of loops defines a second angle of arc between them. Preferably, the first angle is greater than about 30°, and the second angle is less than about half of the first angle. It will be seen that each loop defines an axis, with the angle formed by the axes of adjacent loops being the second angle.

In a third alternative embodiment, the secondary configuration of the microcoil structure forms preferably at least two interconnected equiangular or logarithmic spirals, each defining a single unique axis. As used in this specification, a logarithmic or equiangular spiral is defined as a curve that cuts all radii vectors at a constant angle. Specifically, if the curve is a spiral, that is, a curve in which the radial vector R is a monotonic increasing function of the radial angle θ, the spiral will be an equiangular spiral if the angle α formed between a radial vector R and the tangent for any point P on the spiral is constant. In equiangular spirals having an angle α of greater than about 70°, the configuration begins to resemble that of the shell of the chambered nautilus. In the limiting case, it may be seen that a circle is an equiangular spiral in which the angle α is 90° (the radial vector being a radius).

In a fourth alternative embodiment, the secondary configuration of the microcoil structure resembles a series of interconnected complex curved segments, each of which is defined by a path around the surface of a sphere. Each of the segments is thus defined by a unique focus located at the approximate center point of the sphere around which the path is generated, and by a radius extending from that locus that is equal to the radius of that sphere. Each segment may be defined by radii that are coplanar (in the case of a segment that is defined by a substantially circumferential path around its defining sphere), or by radii that lie in different planes intersecting the sphere (where path around the defining sphere deviates from a circumferential path). The segments thus resemble nearly, but not fully, completed circles (circumferential path) or helical loops (non-circumferential path), and they may be either of uniform or different diameters.

In any of the embodiments, the device is preferably formed from a microcoil structure, but it may alternately be formed of a flexible, filamentous, non-coil structure. Known non-coil structures used in vaso-occlusive devices include, but are not limited to, wires, slotted wires, spiral cut wires, tubes, slotted tubes, spiral cut tubes, polymer filaments, polymer/metal composite filaments, and micro-chains.

In any of the embodiments, the device, in its minimum energy state secondary configuration, has a dimension that is substantially larger (at least about 25% greater) than the largest dimension of the vascular space in which the device is to be deployed. Preferably, the overall length of the device, in its minimum energy state secondary configuration, should be at least about twice, and most preferably about three times, the maximum dimension of the targeted aneurysm or other vascular site in which the device is to be installed. Also, it is advantageous to provide in the device at least one curved segment having a diameter, in the minimum energy state secondary configuration, that is approximately equal to the largest diameter of the targeted aneurysm or vascular site. Thus, when the device is deployed inside a vascular site such as an aneurysm, the confinement of the device within the site causes the device to assume a three-dimensional configuration that has a higher energy state than the minimum energy state. Because the minimum energy state of the device is larger (in at least one dimension) than the space in which it is deployed, the deployed device is constrained by its intimate contact with the walls of the aneurysm from returning to its minimum energy state configuration. Therefore, the device still engages the surrounding aneurysm wall surface, thereby minimizing shifting or tumbling due to blood flow dynamics. Furthermore, the minimum energy state secondary configuration (to which the device attempts to revert) is not one that is conducive to "coin stacking", thereby minimizing the degree of compaction that is experienced.

As will be better appreciated from the detailed description that follows, the present invention provides for effective embolization of vascular structures (particularly aneurysms) having a wide variety of shapes and sizes. It is especially advantageous for use in wide-necked aneurysms. Furthermore, as will be described in more detail below, the present invention may be deployed using conventional deployment mechanisms, such as microcatheters and guidewires.

BRIEF DESCRIPTION OF THE DRAWINGS

FIG. 5 is a plan view of a microcoil vaso-occlusive device in accordance with a first alternative embodiment of the invention;

FIG. 6 is an elevational view of the present invention in the process of being deployed through a microcatheter into a wide-necked aneurysm;

FIG. 8 is a perspective view of a second alternative embodiment of the invention;

FIG. 9 is an elevational view of the second alternative embodiment of FIG. 8;

FIG. 10 is a plan view of another form of the first alternative embodiment of the invention;

FIG. 11 is a plan view of a third alternative embodiment of the invention;

DETAILED DESCRIPTION OF THE INVENTION

Figure 1:
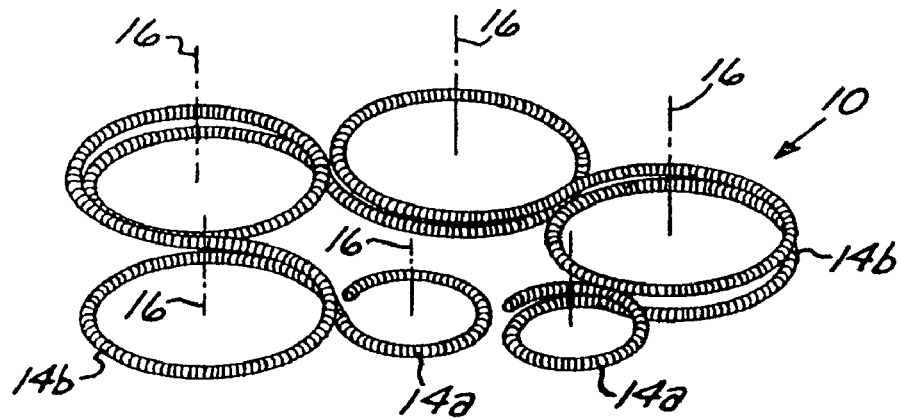
FIG. 1 is a perspective view of a microcoil vaso-occlusive device in accordance with a preferred embodiment of the present invention.
Figure 2:
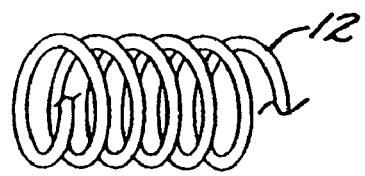
FIG. 2 is a partial view of the device of FIG. 1, taken within the area designated by the numeral 2 in FIG. 1.
Figure 3:
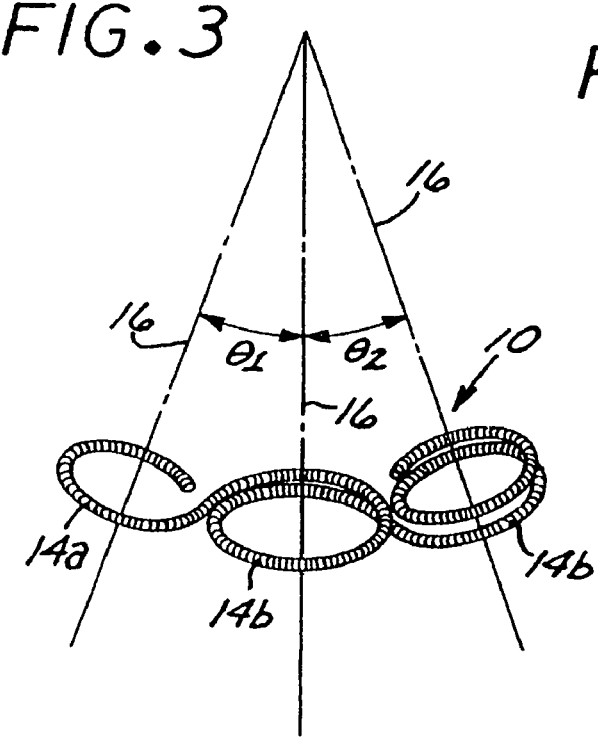
FIGS. 3 and 4 are partial views of a microcoil vaso-occlusive device in accordance with another form of the preferred embodiment of the present invention.
Figure 4:
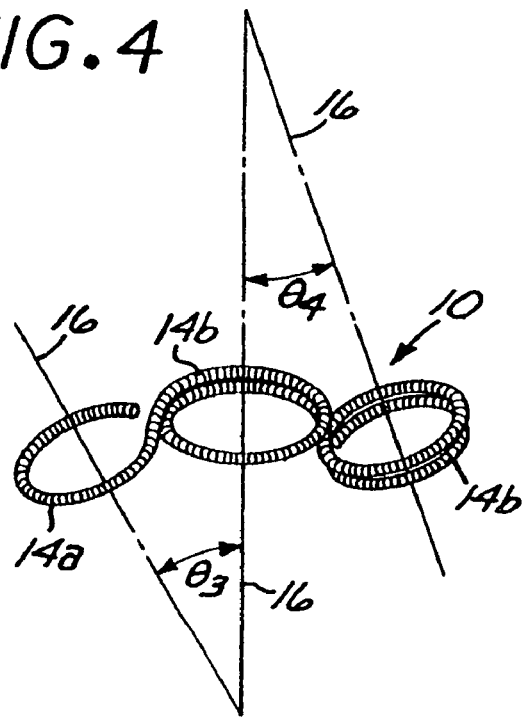

Referring first to FIGS. 1-4 and 8, a microcoil vaso-occlusive device 10, in accordance with a preferred embodiment of the invention is shown. The device 10 comprises a suitable length of wire formed into the primary configuration of a helical microcoil 12 (FIG. 2). Suitable materials for the device 10 include platinum, rhodium, palladium, rhenium, tungsten, gold, silver, tantalum, and various alloys of these metals. Various surgical grade stainless steels may also be used. Preferred materials include the platinum/tungsten alloy known as Platinum 479 (92% Pt, 8% W, available from Sigmund Cohn, of Mount Vernon, N.Y.) and titanium/nickel alloys (such as the titanium/nickel alloy known as "nitinol"). Another material that may be advantageous is a bimetallic wire comprising a highly elastic metal with a highly radiopaque metal. Such a bimetallic wire would also be resistant to permanent deformation. An example of such a bimetallic wire is a product comprising a nitinol outer layer and an inner core of pure reference grade platinum, available from Sigmund Cohn, of Mount Vernon, N.Y., and Anomet Products, of Shrewsbury, Ma. Wire diameters of about 0.0125 mm to about 0.150 mm may be used.

The microcoil 12 has a diameter that is typically in the range of about 0.125 mm to about 0.625 mm, with a preferred a preferred range, for most neurovascular applications, of about 0.25 mm to about 0.40 mm. The axial length of the microcoil 12 may be anywhere from about 5 mm to about 1000 mm, with about 20 mm to about 400 mm being typical.

The primary winding of the microcoil 12 is applied under tension. The amount of tension, and the pitch of the primary winding, determines the stiffness of the microcoil 12. These parameters can be varied along the length of the microcoil 12 to form a microcoil having different degrees of stiffness along its length, which may be advantageous in certain applications.

The microcoil 12 is formed into a minimum energy state secondary configuration that comprises a plurality of curved segments, each defining a unique axis, whereby the microcoil 12 defines multiple axes. More specifically, each of the curved segments defines a plane having an axis that is substantially perpendicular to the plane. In the preferred embodiment of FIGS. 1-4, the curved segments are tangentially-interconnected closed loops 14a, 14b that are substantially circular, and that define a plurality of separate axes 16. In one form of the preferred embodiment, shown in FIG. 1, the loops 14a, 14b are substantially coplanar and define axes 16 that are substantially parallel. In another form of the preferred embodiment, shown in FIGS. 3 and 4, each pair of adjacent loops 14a, 14b defines a shallow angle, whereby their respective axes 16 define an angle ($\theta_1$, $\theta_2$, $\theta_3$, and $\theta_4$) of not more than about 90° between them, and preferably not more than about 45°.

In the above-described embodiment, the microcoil 12 comprises a filamentous structure having proximal and distal ends, wherein the filamentous structure is formed into a minimum energy state secondary configuration comprising a plurality of loops, each defining plane and a unique axis perpendicular to the plane, such that as a path is traced along the filamentous structure from the proximal end to the distal end, the path defines a closed-loop path segment around each of the axes, the path segments alternating between clockwise and counter-clockwise path segments around successive axes.

The preferred embodiment of the invention typically includes a pair of end loops 14a and at least one intermediate loop 14b. Typically, there will be up to four intermediate loops 14b, depending on the vascular site to be embolized, but there may be as many as six or more, for use in very large vascular sites. The intermediate loops are sized to have a diameter approximately equal to the maximum diameter of the target vascular site (e.g., an aneurysm), while the end loops 14a have a slightly smaller diameter (preferably, approximately 1.5 mm smaller), for purposes to be described below.

The primary microcoil 12 is formed into the secondary configuration by heat treatment, as is well known in the art. For example, the annealed primary coil may be initially placed into the secondary configuration by winding or wrapping around a suitably shaped and sized mandrel of refractory material, and then subjected to an annealing temperature for a specified period of time. For Platinum 479, for example, an annealing temperature of about 500° C. to about 1000° C., preferably approximately 670° C., is maintained for about 30 to 90 minutes, preferably about 60 minutes, then cooled to room temperature and ultrasonically cleaned. The resultant secondary configuration is thereby made permanent, and it becomes the minimum energy state configuration of the microcoil 12.

Figure 7:
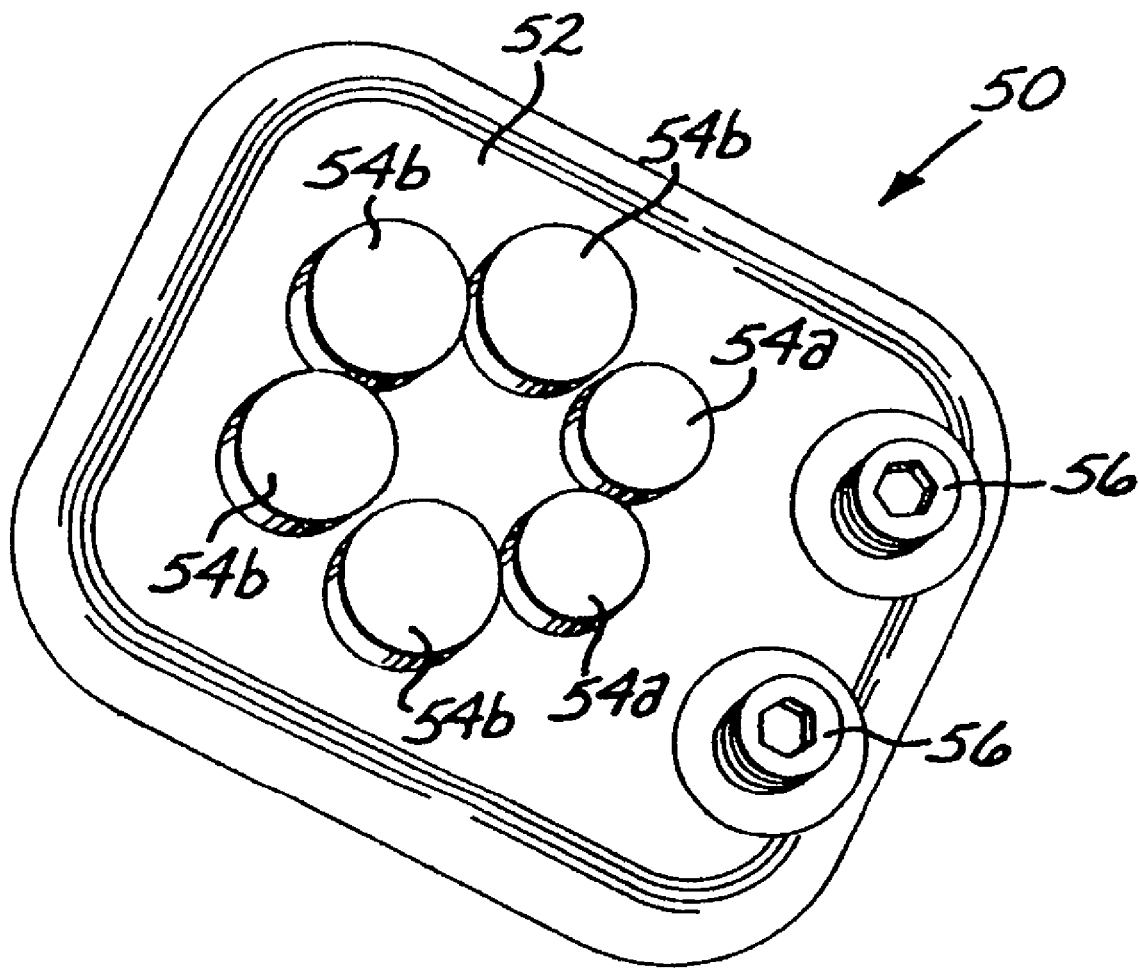
FIG. 7 is a perspective view of a heat treatment fixture used to manufacture the preferred embodiment of the present invention.
Figure 12:
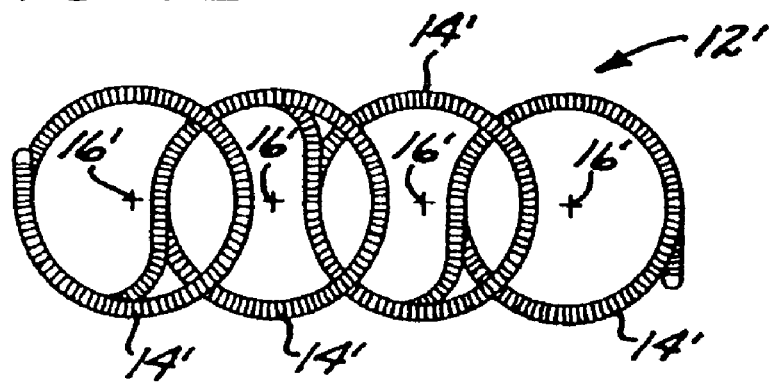
FIGS. 12-15 are plan views of other forms of the preferred embodiment of the invention.

FIG. 7 shows a heat treatment fixture 50 used in the manufacture of the preferred embodiment of the invention. The fixture 50 is made of a refractory material, and it includes a base 52 having a surface on which is provided a mandrel for the secondary winding. The mandrel comprises a plurality of winding pins 54a, 54b extending upwardly from the surface of the base 52. The exemplary fixture 50 shown in the drawing has six pins arranged in roughly a hexagonal pattern. There are two end winding pins 54a adjacent each other, and four intermediate winding pins 54b. A pair of fastening pegs 56 is located near one end of the fixture, for fastening the ends of the primary coil 12.

The diameters of the end winding pins 54a are slightly smaller than the diameters of the intermediate winding pins 54b to achieve the size relationships described above. The spacings between the pins 54a, 54b are only slightly greater than the diameter of the primary coil 12, so that only one wind of the primary coil can be passed around the pins with each winding of the secondary coil. Each subsequent winding of the secondary coil is thus stacked on top of the previous winding. This eliminates any straight sections in the secondary coil, which, during deployment, would tend to push the coil into the parent artery.

During the secondary winding process, the primary coil 12 is kept under tension. The amount of tension can be adjusted to control the degree of spring-back of the loops 14a, 14b of the microcoil 12.

The secondary winding of the microcoil 12 is performed so that the loops 14a, 14b reverse direction as the microcoil 12 is wrapped around each successive pin on the fixture. This ensures that loops will not coin stack, and that they will disperse randomly throughout the aneurysm once deployed. Furthermore, in the preferred embodiment, each loop is wound a complete 360° before the next loop is wound. This ensures that each loop will completely seat within the aneurysm before the microcoil 12 reverses direction. With a complete loop intact, the loop strength is maximized, and the loop distributes loads evenly.

Figure 13:
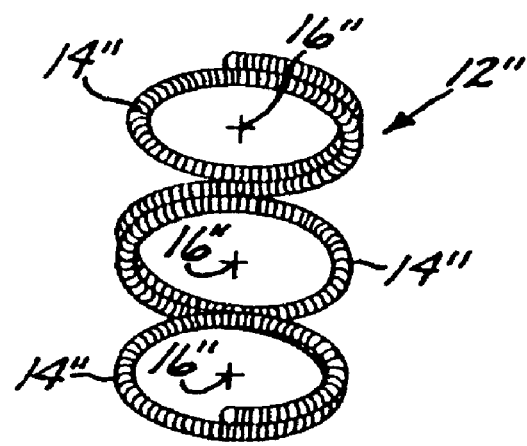
Figure 14:
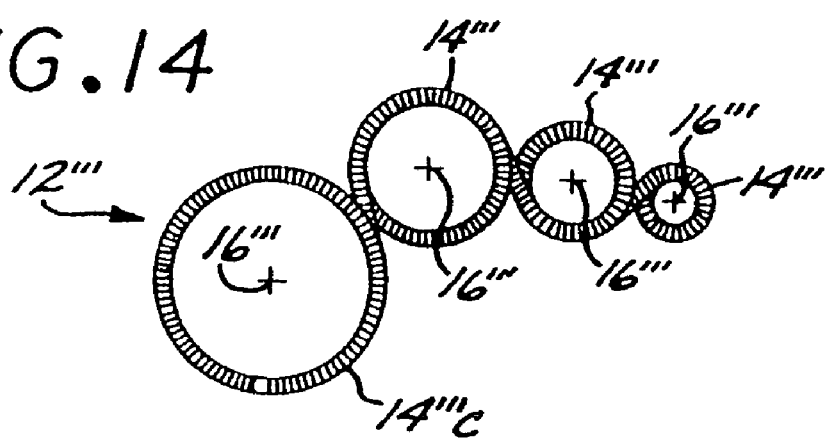
Figure 15:
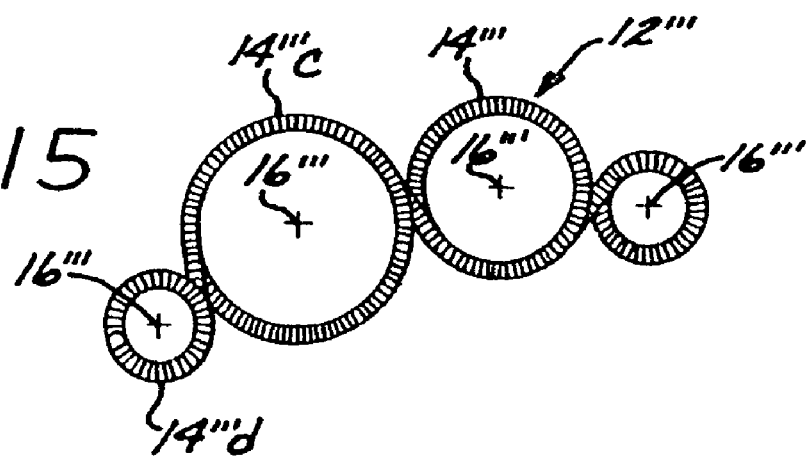

FIGS. 12-15 and 17 illustrate alternative forms of the above-described preferred embodiment. Specifically, in FIG. 12, a microcoil 12' has a secondary configuration that includes a plurality of connected curved segments, wherein the curved segments are overlapping connected closed loops 14', that are substantially circular, with each loop 14' defining a separate axis 16'. In FIG. 13, a microcoil 12" has a secondary configuration that includes a plurality of connected curved segments, wherein the curved segments are tangentially-interconnected, substantially elliptical loops 14", each defining a separate axis 16". FIGS. 14 and 15 show alternative forms that are similar to that of FIGS. 1-4, except that the loops are of different diameters. Thus, in FIG. 14, a microcoil 12''' has a secondary configuration that includes a plurality of tangentially-interconnected, substantially circular loops 14''' of progressively decreasing diameter, starting from a loop 14'''c of the largest diameter, each of the loops defining a unique axis 16'''. The variant form shown in FIG. 15 is similar to that of FIG. 14, except that there is an additional small-diameter loop 14'''d preceding the largest diameter loop 14'''c. A further form of the preferred embodiment, illustrated in FIG. 17, comprises a microcoil $12^{iv}$ having a minimum energy state secondary configuration in which a plurality of interconnected, tangential loops $14^{iv}$ are arranged so that each loop defines an axis $16^{iv}$ that is orthogonal to a unique radius r of a circle, the radii being separated by a fixed angle of arc θ.

FIG. 5 shows a microcoil vaso-occlusion device 20 in accordance with a first alternative embodiment of the invention. This embodiment includes a primary microcoil 22 formed into a secondary minimum energy state configuration that defines a wave-form like structure comprising a longitudinal array of laterally-alternating open loops 24 defining a plurality of separate axes 26. As in the preferred embodiment, the alternative embodiment may be in a first form in which the loops 24 are substantially coplanar and their respective axes 26 are substantially parallel, or in a second form in which each pair of adjacent loops 24 defines a shallow angle, whereby their respective axes 26 define an angle of not more than about 90°, and preferably not more than about 45°, between them. The materials, dimensions, and method of manufacture of this alternative embodiment are, in all material respects, similar to those of the preferred embodiment described above.

FIG. 10 illustrates a specific construction of this embodiment, wherein the primary microcoil structure 22' is formed into a secondary minimum energy state configuration having a wave-form like structure that defines a substantially sinusoidal waveform, defining a plurality of separate axes 26'. The waveform has at least one maximum 22a and at least one minimum 22b, each of which defines an arc of radius r, and wherein each arc is connected to an adjacent arc by a straight section of length L, wherein L is less than about 2r.

The method of using the present invention is shown in FIG. 6. In use, the proximal end of the microcoil 12 (or 22) is attached to the distal end of an elongate delivery device, such as a guidewire or microcatheter (not shown). The attachment may be by any of a number of ways known in the art, as exemplified by the following U.S. patents, the disclosures of which are expressly incorporated herein by reference: U.S. Pat. No. 5,108,407—Geremia et al.; U.S. Pat. No. 5,122,136—Guglielmi et al.; U.S. Pat. No. 5,234,437—Sepetka; U.S. Pat. No. 5,261,916—Engelson; U.S. Pat. No. 5,304,195—Twyford, Jr. et al.; U.S. Pat. No. 5,312,415—Palermo; U.S. Pat. No. 5,423,829—Pham et al.; U.S. Pat. No. 5,522,836—Palermo; U.S. Pat. No. 5,645,564—Northrup et al.; U.S. Pat. No. 5,725,546—Samson; U.S. Pat. No. 5,800,453—Gia; U.S. Pat. No. 5,814,062—Sepetka et al.; U.S. Pat. No. 5,911,737—Lee et al.; U.S. Pat. No. 5,989,242—Saadat et al.; U.S. Pat. No. 6,022,369—Jacobsen et al. U.S. Pat. No. 6,063,100—Diaz et al.; U.S. Pat. No. 6,068,644—Lulo et al.; and U.S. Pat. No. 6,102,933—Lee et al.

A target vascular site is visualized, by conventional means, well-known in the art. When visualized, the vascular site can be measured to determine a known maximum dimension D, which may be its length, width, or depth. The target vascular site may be, for example, an aneurysm 40 branching off a parent artery 42, wherein the aneurysm 40 has a dome 44 connected to the branch artery by a neck 46. A microcoil vaso-occlusive device 12, in accordance with the present invention, is selected that has an overall length, in its minimum energy secondary configuration, that is preferably at least about twice, and more preferably about three times, the determined maximum dimension D of the aneurysm 40. A catheter 30 is passed intravascularly until it enters the dome 44 of the aneurysm 40 via the neck 46. The microcoil 12 is passed through the catheter 30 with the assistance of the guidewire or microcatheter until the microcoil 12 enters the dome 44 of the aneurysm 40.

The undersized end loop 14a at the distal end of the microcoil 12 enters the aneurysm first. This assists in seating the first loop properly, because the smaller size keeps the first loop inside the neck 46 of the aneurysm, avoiding the parent artery 42.

The intermediate loops 14b then enter the aneurysm. Because they are sized to fit the aneurysm, they can deploy freely and smoothly with minimal friction against the wall of the aneurysm. Because the secondary configuration of the microcoil 12 is essentially coplanar, all of the intermediate loops exert a force against the walls of the aneurysm dome 44, thereby improving the resistance of the microcoil 12 to shifting due to pulsatile blood flow.

As the microcoil 12 enters the aneurysm, it attempts to assume its secondary configuration. Because the microcoil, in its secondary configuration, has an overall length that is substantially greater than the maximum dimension D of the aneurysm 40, however, it is constrained into a deployed configuration in which it tends to line the periphery of the aneurysm. In this deployed configuration, the microcoil is in an energy state that is substantially higher than its minimum energy state. Thus, when the device is deployed inside a vascular site such as an aneurysm, the confinement of the device within the site causes the device to assume a three-dimensional configuration that has a higher energy state than the minimum energy state. Because the minimum energy state of the device is larger (in at least one dimension) than the space in which it is deployed, the deployed device is constrained by its intimate contact with the walls of the aneurysm from returning to its minimum energy state configuration. Therefore, the device still engages the surrounding aneurysm wall surface, thereby minimizing shifting or tumbling due to blood flow dynamics. Furthermore, the minimum energy state secondary configuration (to which the device attempts to revert) is not one that is conducive to "coin stacking", thereby minimizing the degree of compaction that is experienced.

The undersized end loop 14a at the proximal end of the microcoil 12 enters the aneurysm last. After the microcoil is fully deployed, it is controllably detached from the delivery device by any suitable means well-known in the art, thereby allowing the delivery device to be withdrawn, leaving the microcoil in place to embolize the aneurysm. After detachment, the proximal end loop 14a curls into the neck 46 of the aneurysm 40, avoiding the parent artery 42.

The microcoil is designed with a maximum loops diameter that is dimensioned to line the periphery of the aneurysm upon deployment, as mentioned above. For larger aneurysms, it is advantageous to fill in a substantial portion of the interior volume of the aneurysm by deploying one or more additional microcoils, of progressively smaller maximum loop diameter.

FIGS. 8 and 9 illustrate a vaso-occlusion device in accordance with a second alternative embodiment of the invention. This embodiment includes a primary microcoil 60 formed into a secondary minimum energy state configuration that forms a series of tangential closed loops 62 (preferably substantially circular or elliptical), wherein the entire structure subtends a first angle of arc $\theta_1$, and wherein each adjacent pair of circles or ellipses defines a second angle of arc $\theta_2$ between them. Preferably, the first angle $\theta_1$ is greater than about 30°, and the second angle $\theta_2$ is less than about half of the first angle $\theta_1$. Although not illustrated in the drawings, it will be appreciated that each loop 62 defines an axis, whereby the angle formed between the axes of adjacent loops 62 is equal to $\theta_2$.

FIG. 11 illustrates a vaso-occlusive device in accordance with a third alternative embodiment of the invention. In this embodiment, a microcoil 70 has a secondary configuration that forms at least a pair of connected equiangular or logarithmic spirals 72, each of the spirals defining an axis 73 that is orthogonal to the plane defined by the spiral. For the purpose of this specification, an equiangular or logarithmic spiral is defined as a curve that cuts all radii vectors at a constant angle, where a radial vector R is defined as a line drawn from any point P on the spiral to the center of the spiral. Specifically, if the curve is a spiral, that is, a curve having a radial vector R that is a monotonic increasing function of the radial angle $\theta$, the spiral will be an equiangular spiral if the angle $\alpha$ formed between a radial vector and the tangent for any point P on the spiral is constant.

Figure 16:
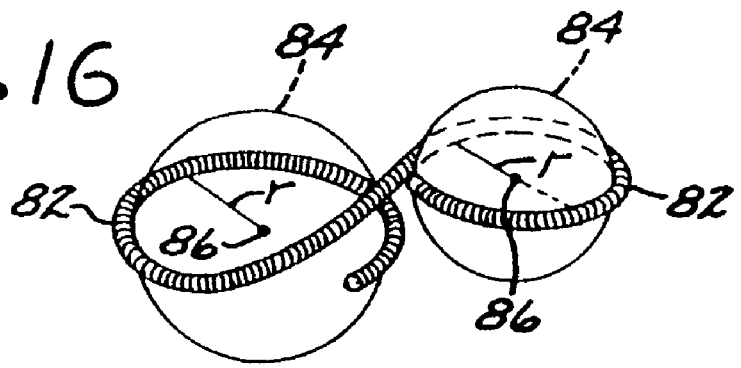
FIG. 16 is a perspective view of a fourth alternative embodiment of the invention, showing how it is formed on a specialized heat treatment fixture, the latter being shown in a simplified, idealized form.
Figure 17:
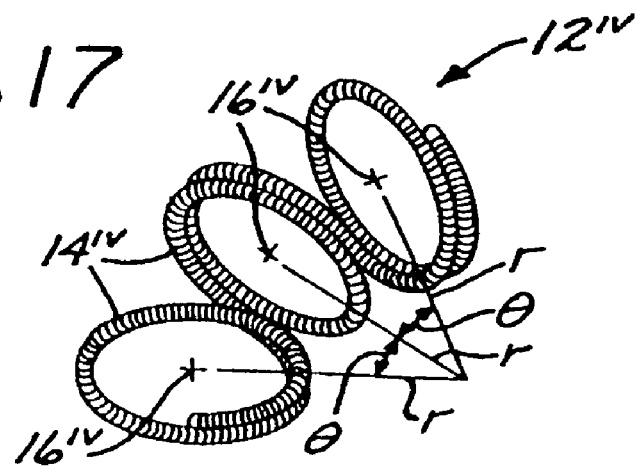
FIG. 17 is an elevational view of still another form of the preferred embodiment of the present invention.

FIG. 16 illustrates a vaso-occlusive device in accordance with a fourth alternative embodiment, wherein a microcoil 80 has a secondary configuration that resembles a series of interconnected complex curved segments 82, each of which is defined by a path around the surface of a sphere 84. Each of the segments is thus defined by a unique focus 86 located at the approximate center point of the sphere 84 around which the path is generated, and by a radius r extending from that locus 86 that is equal to the radius of that sphere. Each segment may be defined by radii that are coplanar (in the case of a segment that is defined by a substantially circumferential path around its defining sphere), or by radii that lie in different planes intersecting the sphere (where path around the defining sphere deviates from a circumferential path). The segments thus resemble nearly, but not fully, completed circles (circumferential path) or helical loops (non-circumferential path), and they may be either of uniform or different diameters.

The present invention thus exhibits several advantages over prior art three-dimensional microcoils. For example, there is increased coverage of the aneurysm neck, due to the presence of loops across the neck, yet the probability of any part of the device intruding into the parent artery is reduced. The secondary coil configuration also provides smoother deployment, and, once deployed, the device exhibits greater resistance to coil compaction, thereby increasing positional stability in the face of pulsatile blood flow. This stability is achieved with lower overall friction between the device and the aneurysm wall. Moreover, the random distribution of loops throughout the aneurysm allows the device to maintain a complex shape inside the aneurysm, yielding improved embolization.

While a preferred embodiment and alternative embodiments of the invention have been described herein, it will be appreciated that a number of variations and modifications will suggest themselves to those skilled in the pertinent arts. For example, other secondary configurations than those described herein may be found that will yield most, if not all, of the significant advantages of the invention for treatment of the typical aneurysm, or that will prove especially advantageous in specific clinical applications. Also, for specific applications, the dimensions and materials may be varied from those disclosed herein if found to be advantageous. These and other variations and modifications are considered to be within the spirit and scope of the invention, as defined in the claims that follow.

What is claimed is:

1. A vaso-occlusive device for embolizing a vascular site having a known maximum dimension, wherein the device comprises a filamentous structure formed into a minimum energy state secondary configuration comprising a plurality of curved segments defining a plurality of inflection points,
   wherein each of the curved segments in the series of at least three curved segments defines a discrete axis;
   wherein the curved segments are substantially closed loops, interconnected to each other;
   wherein each of the curved segments in the series of at least three curved segments has a diameter; and
   wherein the device, in its minimum energy state secondary configuration, has an overall length that is at least about twice the diameter of at least on eof the curved segments in the series of at least three curved segments.

2. The device of claim 1, wherein the curved segments are substantially circular loops.

3. The device of claim 1, wherein each of the curved segments defines a plane and an axis that is substantially perpendicular to the plane.

4. The device of claim 1, wherein the multiple axes are substantially parallel.

5. The device of claim 1, wherein each adjacent pair of the multiple axes forms an acute angle.

6. A filamentous vaso-occlusive device having a minimum energy state secondary configuration comprising a plurality of tangentially-interconnected loops, each defining a plane and a unique axis perpendicular to the plane, wherein the device has a proximal end and a distal end and defines a substantially continuously-curved structure between the proximal and distal ends.

7. The device of claim 6, wherein at least two of the unique axes of the tangentially-interconnected loops are nonparallel.

8. The device of claim 6, wherein the overall length is at least about three times the known maximum dimension of the vascular site.

9. A method of embolizing a vascular site, comprising the steps of:
   (a) determining a maximum dimension for the vascular site;
   (b) providing vaso-occlusive device comprising a filamentous structure formed into a minimum energy state secondary configuration comprising a series of at least three interconnected curved segments defining a plurality of inflection points, wherein each of the curved segments is a substantially closed loop, each defining a discrete axis, whereby the device, in its minimum energy state configuration, has a length that is at least about twice the maximum dimension of the vascular site; and
   (c) deploying the device into the interior of the vascular site so that device is contained within the vascular site in a configuration having an energy state that is substantially higher than its minimum energy state, whereby the device is constrained by its contact with the vascular site from returning to its minimum energy state configuration.

10. The method of claim 9, wherein the device, in its minimum energy state secondary configuration, has at least one curved segment having a diameter that is approximately equal to the maximum dimension of the vascular site.

11. The method of claim 9, wherein the device, in its minimum energy state configuration, has a length that is at least about three times the maximum dimension of the vascular site.

* * * * *